(12) United States Patent
Takahashi et al.

(10) Patent No.: US 12,339,285 B2
(45) Date of Patent: Jun. 24, 2025

(54) METHOD FOR ESTIMATING THERAPEUTIC EFFICACY

(71) Applicant: Konica Minolta, Inc., Tokyo (JP)

(72) Inventors: Masaru Takahashi, Kokubunji (JP); Yasuyuki Motokui, Kunitachi (JP); Noboru Koyama, Niiza (JP)

(73) Assignee: KONICA MINOLTA, INC., Tokyo (JP)

( * ) Notice: Subject to any disclaimer, the term of this patent is extended or adjusted under 35 U.S.C. 154(b) by 663 days.

(21) Appl. No.: 16/491,768

(22) PCT Filed: Mar. 9, 2018

(86) PCT No.: PCT/JP2018/009199
§ 371 (c)(1),
(2) Date: Sep. 6, 2019

(87) PCT Pub. No.: WO2018/164262
PCT Pub. Date: Sep. 13, 2018

(65) Prior Publication Data
US 2020/0371106 A1    Nov. 26, 2020

(30) Foreign Application Priority Data

Mar. 10, 2017 (JP) ................................ 2017-046234

(51) Int. Cl.
| | | |
|---|---|---|
| G01N 33/574 | (2006.01) | |
| A61B 5/00 | (2006.01) | |
| C12Q 1/6804 | (2018.01) | |
| G16B 25/00 | (2019.01) | |
| G16B 45/00 | (2019.01) | |
| G16H 20/00 | (2018.01) | |
| G16H 20/10 | (2018.01) | |
| G16H 30/00 | (2018.01) | |

(52) U.S. Cl.
CPC ..... *G01N 33/57492* (2013.01); *A61B 5/4848* (2013.01); *C12Q 1/6804* (2013.01); *G16H 20/10* (2018.01); *A61B 2503/40* (2013.01); *A61B 2503/42* (2013.01); *G01N 2333/71* (2013.01); *G16B 25/00* (2019.02); *G16B 45/00* (2019.02); *G16H 20/00* (2018.01); *G16H 30/00* (2018.01)

(58) Field of Classification Search
None
See application file for complete search history.

(56) References Cited

U.S. PATENT DOCUMENTS

2017/0141987 A1    5/2017  Amulothu et al.

FOREIGN PATENT DOCUMENTS

| JP | 2011209101 A | 10/2011 |
|---|---|---|
| JP | 2014532184 A | 12/2014 |
| JP | 2016510748 A | 4/2016 |
| JP | 2017500028 A | 1/2017 |
| JP | 2017026375 A | 2/2017 |
| WO | 2012029752 A1 | 3/2012 |
| WO | 2012133047 A1 | 4/2012 |
| WO | 2013035703 A1 | 3/2013 |
| WO | 2016041932 A1 | 3/2016 |
| WO | 2017141987 A1 | 8/2017 |
| WO | 2018030193 A1 | 2/2018 |

OTHER PUBLICATIONS

Byrne et al., "Interrogating open issues in cancer precision medicine with patient-derived xenografts", (2017) Nature Perspectives 17: 254-268 (Year: 2017).*
Zhang et al. Patient-derived xenografts of triple-negative breast cancer reproduce molecular features of patient tumors and respond to mTOR inhibition. Breast Cancer Research 2014, 16:R36, pp. 1-16 (Year: 2014).*
Yezhelyev et al. In Situ Molecular Profiling of Breast Cancer Biomarkers with Multicolor Quantum Dots. Adv. Mater. 2007, 19, 3146-3151 (Year: 2007).*
Tolaney et al. Role of vascular density and normalization in response to neoadjuvant bevacizumab and chemotherapy in breast cancer patients. PNAS 2015, vol. 112, No. 46, pp. 14325-14330 and Supplementary Information, pp. 1-12 (Year: 2015).*
International Search Report corresponding to Application No. PCT/JP2018/009199; Dated Jun. 12, 2018.
Jeffrey J. Wallin et al., "Atezolizumab in combination with bevacizumab enhances antigen-specific T-cell migration in metastatic renal cell carcinoma," Nature Communications; vol. 7, 2016, 8 pages.
V. Papadimitrakopoulou et al., "The Battle-2 Study: A Biomarker-Integrated Targeted Therapy Study in Previously Treated Patients With Advanced Non-Small-Cell Lung Cancer," Journal of Clinical Oncology; 2016; vol. 34, pp. 3638-3647.
Wolfgang Jager et al., "Patient-derived bladder cancer xenografts in the preclinical development of novel targeted therapies," Oncotarget, vol. 6, No. 25, 2015; pp. 21522-21532.
Written Opinion of the International Searching Authority corresponding to Application No. PCT/JP2018/009199; Dated Jun. 12, 2018.
JPOA Notice of Reasons for Refusal for corresponding JP Application No. 2019-503867; Issued on Sep. 7, 2021.
JPO Notice of Reasons for Refusal for corresponding JP Application No. 2019-503867, Issued on Feb. 8, 2022.
Byrne, A., et al. "Interrogating open issues in cancer precision medicine with patient-derived xenografts". Nat Rev Cancer vol. 17, pp. 254-268. (Dated: Jan. 20, 2017).
Hidalgo M., et al. "Patient-derived xenograft models: an emerging platform for translational cancer research". Cancer Discovery, vol. 4, No. 9, pp. 998-1013. (Dated Jul. 15, 2014).

(Continued)

*Primary Examiner* — G. Steven Vanni
(74) *Attorney, Agent, or Firm* — CANTOR COLBURN LLP

(57) ABSTRACT

Disclosed herein is a method including: acquiring one or more pieces of information including information about expression status of a specific biomarker in a lesion collected from a human by using a laboratory animal transplanted with the lesion; and using the information to estimate therapeutic efficacy through analysis.

8 Claims, 3 Drawing Sheets

(56) References Cited

OTHER PUBLICATIONS

Zhou L., et al. "Quantum Dot-based Immunohistochemistry for Pathological Applications". Cancer Translational Medicine, vol. 2, No. 1; pp. 2:21-8. (Dated Jan. 1, 2016).
EPO Extended European Search Report for corresponding EP Application No. 18764071.9, dated Feb. 10, 2020.

* cited by examiner

PATTERNS OF LOCALIZATION

LOCALIZATION A      LOCALIZATION B      LOCALIZATION C

METHOD FOR ESTIMATING THERAPEUTIC EFFICACY

CROSS REFERENCE TO RELATED APPLICATIONS

This is the U.S. national stage of application No. PCT/JP2018/009199, filed on Mar. 9, 2018. Priority under 35 U.S.C. § 119(a) and 35 U.S.C. § 365(b) is claimed from Japanese Application No. 2017-046234, filed Mar. 10, 2017; the disclosures of which are incorporated herein by reference.

TECHNICAL FIELD

The present invention relates to a method for estimating the efficacy of a drug or a therapy by mainly using laboratory animals.

BACKGROUND ART

In the development of a cancer therapeutic drug, the efficacy of a drug candidate is usually verified by actually administering it to patients in a clinical trial (drug trial, clinical study). For example, a method is disclosed in which tumor tissue is collected from a patient before and after drug administration and immunostained to compare a change in protein expression before and after drug administration (Non-Patent Literature 1 (FIG. 3)). However, an experimental system targeted to patients absolutely requires the cooperation of many patients, and needs the involvement of doctors because a drug is actually administered to patients. Further, it can be said that a heavy burden is placed on patients because there is a risk for the occurrence of an unexpected side effect or the like. In order to reduce such a risk or burden, there has been a demand for a means for previously estimating the effect, side effect, or the like of a drug at the time when the drug is actually administered to clinical samples (patients) by previously performing a verification test in an environment close to clinical samples (patients) before a trial is actually performed on patients.

In order to meet such a demand, a model animal produced by transplanting human-derived cancer (tumor) cells or tissue into a laboratory animal, for example, a tumor-bearing mouse produced using a mouse as a laboratory animal is sometimes used as an experimental system that re-creates the environment in the body of a cancer patient. The use of such a tumor-bearing mouse makes it possible to verify the effect or safety (toxicity) of a drug or a candidate substance thereof in an environment relatively close to that in a human even in the stage of a drug discovery research or a non-clinical trial performed before a trial targeted to humans.

Examples of a known tumor-bearing mouse include a cultured cancer cell-transplanted mouse produced by transplanting cultured cells into a mouse and growing them in the mouse and a patient-derived tumor tissue-transplanted mouse produced by transplanting tumor tissue or tumor cells collected from a patient into a mouse and growing it or them in the mouse.

A cultured cancer cell-transplanted mouse is produced using cultured cells obtained by culturing and cloning tumor cells collected from a patient in a test tube. Such cultured cells can easily be transplanted into a mouse, and therefore a cultured cancer cell-transplanted mouse can relatively easily be produced. Further, a mouse transplanted with cloned cultured cells inherits clonal elements, and therefore a plurality of tumor-bearing mice having smaller individual differences can be produced. Because of such advantages, cultured cancer cell-transplanted mice have classically been recognized as established laboratory animals.

On the other hand, a patient-derived tumor-transplanted mouse has recently come to be widely used, which is produced by transplanting tumor tissue (tumor site) or tumor cells collected from a patient in a mouse. For example, a patient-derived tumor tissue-transplanted mouse prepared by transplanting patient (human)-derived tumor tissue into a mouse with acquired immune deficiency and growing it in the body of the mouse or the like for a certain period of time is called a PDX (Patient-derived tumor xenograft) model mouse.

It has been determined that patient-derived tumor-transplanted mice more stably maintain the complexity of cancer cells (including the origin of cancer cells (e.g., genetic mutations)) beyond generations as compared to cultured cancer cell-transplanted mice, and high reliability and reproducibility of a test has been recognized.

For example, diagnostic or therapeutic methods (methods for obtaining an index for diagnosis or therapy) have come to actively be developed on the basis of a non-clinical test method using PDX model mice. It has been considered that a test using PDX model mice can evaluate the effect or safety of a drug in a model that highly re-creates the actual disease state of a human, that is, in an environment close to that of the lesion of a human.

Non-Patent Literature 2 discloses an IHC (immunohistochemical) method that evaluates the expression levels of proteins in the tumor tissue of a PDX model mouse. As a staining technique used in an IHC method, a method is used in which an enzyme-labeled antibody is bound to a target protein (antigen) by a direct or indirect method, and then a substrate is reacted with the enzyme to develop a color. For example, DAB staining using peroxidase and diaminobenzidine is widely used.

However, in the case of enzymatic staining such as DAB staining used in an IHC method, the depth of color greatly depends on environmental conditions such as temperature and time, and therefore there is a problem that it is difficult to accurately estimate the actual amount of an antigen or the like from the depth of color. Further, as shown in Non-Patent Literature 2, evaluation is often performed according to several grade scores on the basis of the depth of color or the like, and is therefore closer to qualitative evaluation rather than quantitative evaluation.

A "qualitative" technique refers to a method in which the expression level of a protein, the number of cells expressing a protein, or the like or an index value closely related thereto is not directly used, but evaluation is performed according to several grade scores on the basis of a number or index value within a predetermined range which correlates with the expression level of a protein, the number of cells expressing a protein, or the like, and typically refers to a technique based on subjective and empirical elements of an observer. For example, an IHC method using DAB staining to evaluate HER2 protein expressed on the cell membranes of breast cancer cells or the like according to four-grade scores on the basis of stainability and staining intensity (staining pattern) ("Third edition of Guidelines for HER2 testing", established by Pathological Committee for optimal use of trastuzumab, September 2009) corresponds to a "qualitative" technique.

On the other hand, a "quantitative" technique refers to a technique in which the expression level of a protein or the number of cells expressing a protein or an index value closely related thereto is directly used, and typically refers to a technique in which evaluation is performed on the basis of objective measurement results using a device.

In current studies of academia, as shown in Non-Patent Literature 2, the expression levels of proteins in tumor tissues of patients and PDX mice are merely qualitatively analyzed by an IHC (immunohistochemical) method. Further, companies such as those providing mice and those providing test services and medical institutions such as hospitals have little interest in accurately evaluating the expression levels of proteins. That is, it can be said that the technical significance of quantitatively and accurately determining the expression levels of proteins or the like in tumor tissues or the like of PDX mice is yet unknown.

In recent years, a method for labeling a protein has been proposed and studied for practical use, which uses nano-sized fluorescent particles, for example, particles obtained by integrating a phosphor, such as a fluorescent dye or a quantum dot, in a matrix such as a resin (Phosphor Integrated Dots: PIDs). By labeling a target protein with phosphor integrated dots and irradiating them with exciting light suitable for the fluorescent substance, the protein can be observed as bright spots having high brightness, and therefore the amount of the expressed protein can be quantitatively evaluated. For example, WO2012/029752 (Patent Literature 1) and WO2013/035703 (Patent Literature 2) disclose methods in which immunostaining of a target protein is performed using phosphor integrated dots (also referred to as fluorescent substance-integrated nanoparticles). Such fluorescent nanoparticles such as PIDs are less likely to discolor, and therefore observation and imaging can be performed for a relatively long time. Further, the positions of a target protein can be indicated with a high degree of accuracy due to high brightness of the fluorescent nanoparticles.

In recent years, the accuracy and result analysis of a genetic test of tumor tissue have significantly been improved. Therefore, gene-based analysis has also come to be actively performed in addition to the above-described protein-based verification. For example, analyses of genetic mutations specific to tumor tissue, and researches about the expression status of specific biological molecules (protein or RNA) related thereto and results thereof are publicly available. For example, Non-Patent Literature 3 suggests the possibility that the effect of a therapy or a drug can be estimated on the basis of information derived from tumor tissue genetic mutations.

Under such circumstances, clinical sites for new drug development have come to pay attention to estimating the effect of a drug mainly on the basis of gene information to stratify patients who will receive the effect of the drug. Further, successful cases using a developed approach called Precision Medicine have come to be reported. Precision Medicine is an approach in which the effect of a drug or a therapy is estimated on the basis of gene information to perform preventive measures, an examination, or a therapy suitable for each person. However, it is impossible to say that genetic mutations follow only Mendel's law of heredity, and can occur after birth by factors such as radiation, foods, aging, infective diseases, and autoimmunity. Therefore, there is an extreme opinion that the profile of genetic mutations is different from person to person, and it is also suggested that in order to estimate the effect of a therapy or a drug on the basis of information derived from genetic mutations, the effect needs to be derived from large amounts of gene information (genetic mutation information).

CITATION LIST

Patent Literatures

Patent Literature 1: WO2012/029752
Patent Literature 2: WO2013/035703

Non-Patent Literatures

Non-Patent Literature 1: Nature Communications, 2016; Vol. 7, 12624
Non-Patent Literature 2: Oncotarget, 2015; Vol. 6, No. 25, 21522-21532 Non-Patent Literature 3: Journal of Clinical Oncology 2016; 34:3638-3647.

SUMMARY OF INVENTION

Technical Problem

As described above, there is a possibility that the effect of a therapy or a drug can be estimated by identifying a biological molecule specific to tumor tissue (hereinafter referred to as a specific biomarker) from gene information acquired by a genetic test of the tumor tissue. However, gene information merely suggests the possibility that a specific biomarker related to the gene is expressed, and does not demonstrate the expression of the specific biomarker. That is, it is impossible to determine, only from the result of a genetic test, that a specific biomarker is actually expressed or the specific biomarker is actually involved in, for example, the medicinal effect of a drug.

In view of the above-described problem, it is an object of the present invention to provide a means in which information about the expression status of a specific biomarker is acquired and analyzed using a laboratory animal transplanted with the lesion (diseased tissue) of a human to estimate a possible therapeutic effect, side effect, or the like at the time when a patient is actually treated.

Solution to Problem

In order to achieve the above object, the present invention takes the following measures. That is, the gene information (genetic mutation information) of diseased tissue (lesion) collected from a human (e.g., a patient, a clinical sample) is analyzed to identify a specific biomarker (e.g., protein, RNA, miRNA) related to mutation information specific to the human. Further, the expression status of the specific biomarker in the diseased tissue transplanted into a laboratory animal is identified. A preferred example of a means for identifying such an expression status is fluorescent staining using fluorescent nanoparticles such as phosphor integrated dots. An image of the fluorescently-stained diseased tissue is captured to acquire image information about the expression status of the specific biomarker so that the expression status can be quantitatively measured, observed, and analyzed. The present inventors have found that the effect, efficacy, or the like of a therapy or medication in the treatment and clinical trial (drug trial, clinical study) of each patient can be estimated by analyzing information about the expression status of a specific biomarker in such a manner as described above.

More specifically, one aspect of the present invention provides a method in which information about the expression status of a specific biomarker in diseased tissue collected from a human and transplanted into a laboratory animal is acquired, the efficacy of a therapy in the laboratory animal is evaluated (a second-order effect such as a side effect as well as efficacy is also evaluated), and the information about expression status is linked to the evaluation to estimate efficacy in a clinical trial (drug trial) or a therapy to be actually performed on the human with a high degree of accuracy.

Another aspect of the present invention provides a method in which a database is constructed by integrating, as a series of information, such information about the expression status of a specific biomarker, analysis results thereof, and medicinal information, and efficacy in a clinical trial (drug trial) or a therapy is estimated with a high degree of accuracy using the database.

Advantageous Effects of Invention

According to the present invention, it is possible to estimate the efficacy of a drug or a therapy with accuracy higher than ever before by analyzing information about the expression status of a specific biomarker from many directions using a human diseased tissue (lesion)-bearing laboratory animal.

Further, a therapeutic method or a drug expected to be effective can appropriately be selected by performing a surrogate test using a laboratory animal before a clinical trial, a drug trial, or a therapy is actually performed, and therefore a more effective therapy can be performed so that medical economical effects such as period shortening, cost saving, and success probability increase can also be expected.

DESCRIPTION OF EMBODIMENTS

Figure 1:
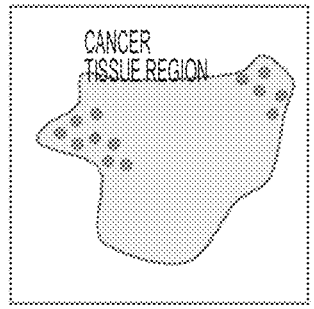
FIG. 1 shows the distribution pattern of a specific biomarker as a piece of information about the expression status of the specific biomarker, in which Patten A schematically shows a state where the specific biomarker is localized to form colonies in the periphery of a tumor tissue region, Pattern B schematically shows a state where the specific biomarker is localized to form a band in the periphery of a tumor tissue region, and Pattern C schematically shows a state where the specific biomarker is localized to form a colony in the central area of a tumor tissue region.
Figure 1:
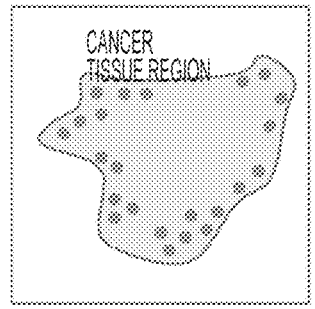
Figure 1:
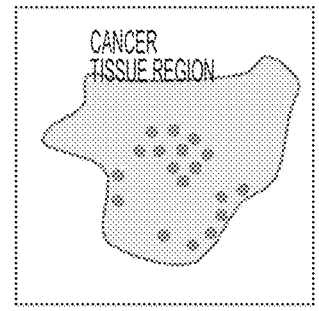
Figure 2:
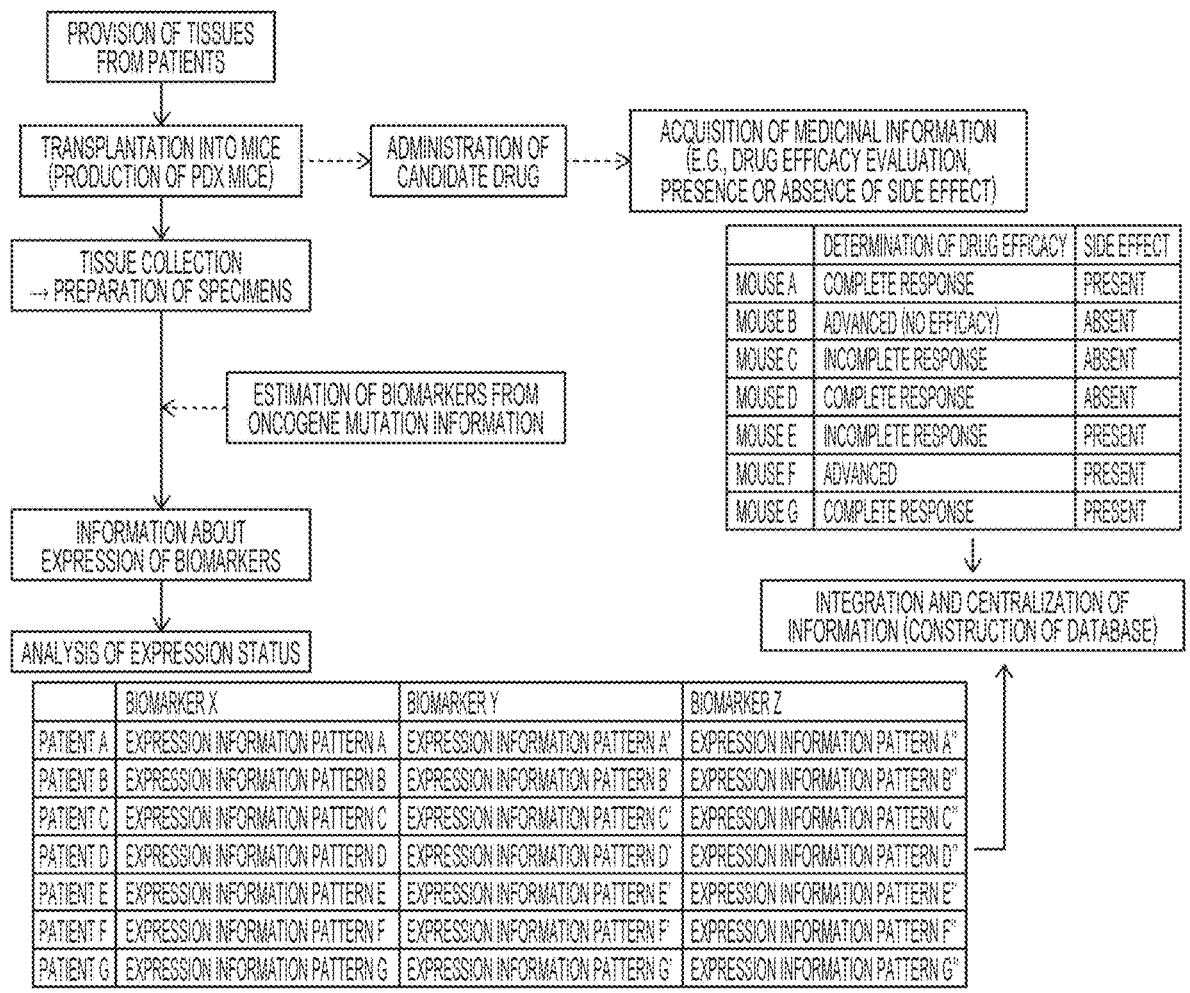
FIG. 2 is a block diagram for constructing a database in which one or more information groups including information about the expression status of a specific biomarker are integrated.
Figure 3:
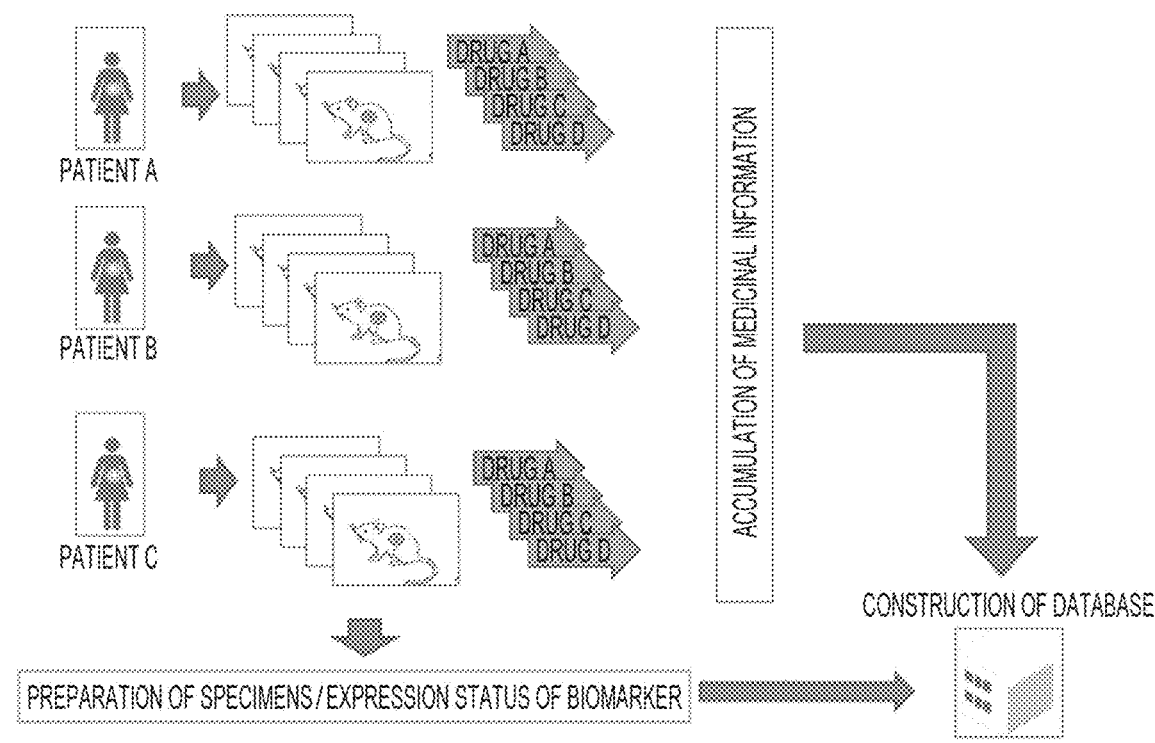
FIG. 3 is a schematic diagram for constructing a database.
Figure 4:
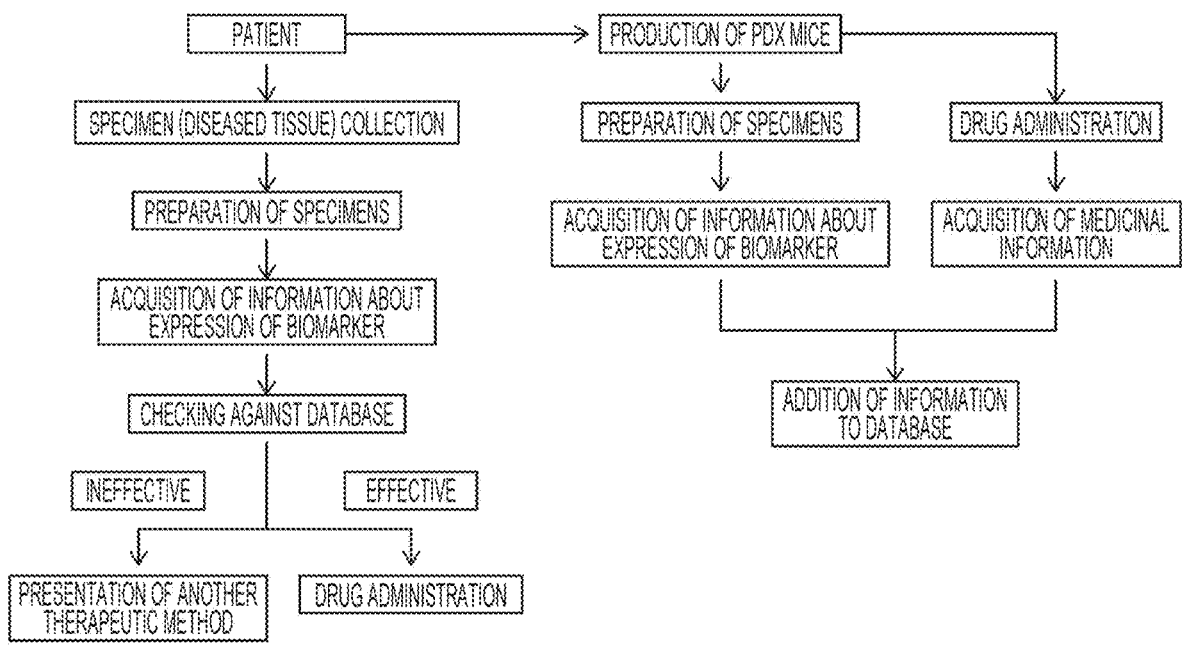
FIG. 4 is a block diagram showing an example of a method for estimating the efficacy of a therapy by utilizing a database.
Figure 5:
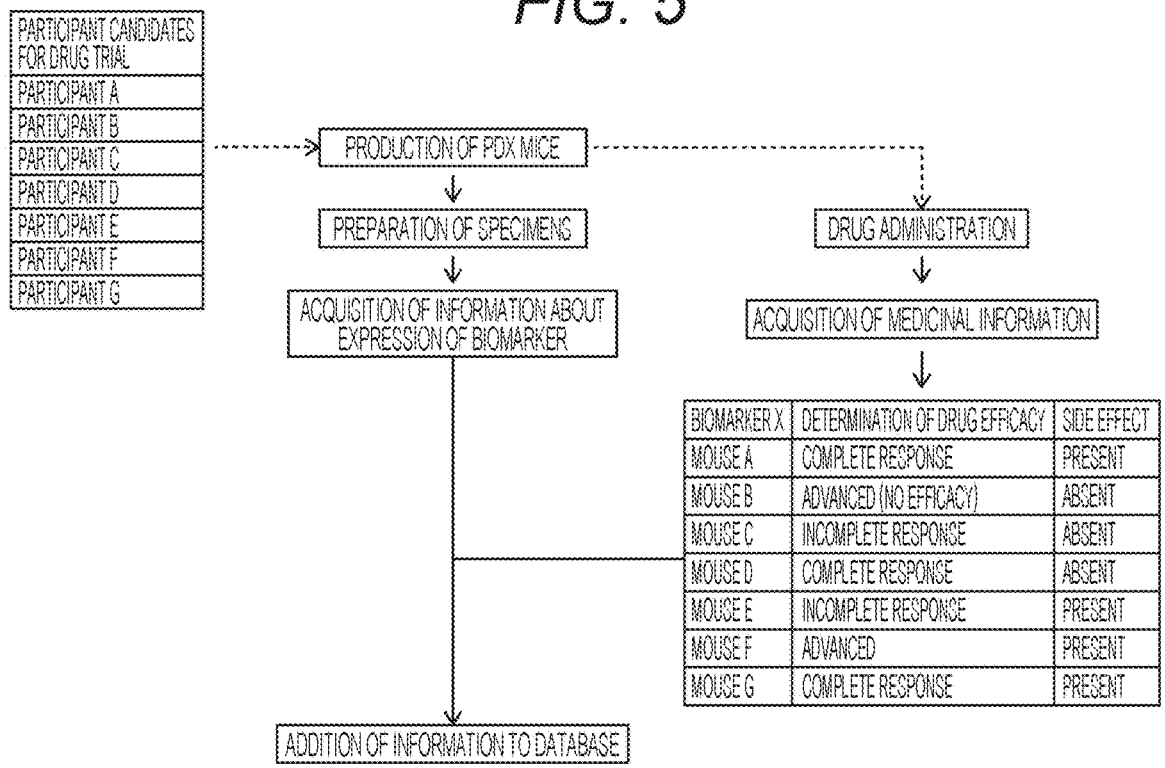
FIG. 5 is a block diagram showing an example of a method for utilizing a database in a drug trial.
Figure 6:
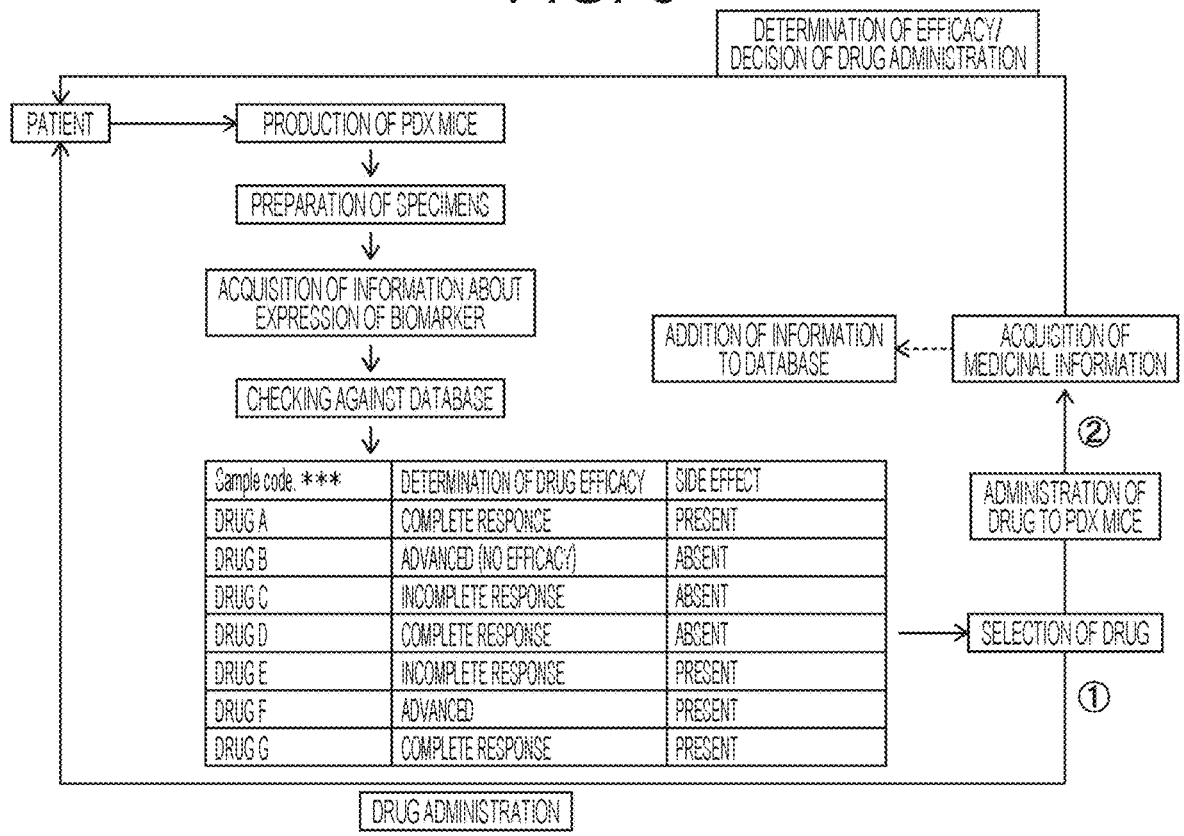
FIG. 6 is a block diagram showing an example of a method for selecting a therapeutic strategy by utilizing a database.

The present invention includes a method including: acquiring one or more pieces of information including information about a specific biomarker that will be described later by using, as a specimen, a lesion collected from a human; and using the information to estimate efficacy of a therapy.

Another aspect of the present invention includes a method including: acquiring one or more pieces of information including information about expression status of a specific biomarker by using, as a specimen, a lesion collected from a transplant site in a laboratory animal transplanted with tissue of a lesion collected from a human or cells derived therefrom; and using the information to estimate efficacy of a therapy.

Yet another aspect of the present invention includes a method including: acquiring one or more pieces of information including information about expression status of a specific biomarker by using, as a specimen, a lesion collected from a human; acquiring one or more pieces of information including information about expression status of a specific biomarker by using, as a specimen, a lesion collected from a transplant site in a laboratory animal transplanted with tissue of the lesion collected from the human or cells derived therefrom; and using these acquired pieces of information in combination to estimate efficacy of a therapy.

In addition to the information about expression status of a specific biomarker, the above-described information may include, for example, information about morphology of cells expressing the specific biomarker or expression status of another biological molecule, or information other than information about cells expressing the specific biomarker, such as a vascular occupancy in the specimen.

In the present invention, the "human" refers to a human having a disease (e.g., cancer) as a target of a therapy which will be described later or a human suspected to have a disease. In this description, the "human" is sometimes referred to as a patient. It is to be noted that the "having a disease" means that the human has been diagnosed with a disease by a doctor or the like, and the "suspected to have a disease" means that the human has been judged to have the possibility of a disease by a certain known technique.

The "lesion" refers to a site that usually changes due to the occurrence or progression of a disease, and includes diseased tissue, but may include also surrounding normal tissue. For example, the "lesion" in a cancer patient refers to a tumor site (or a site suspected to have tumor), and may include tumor tissue and surrounding normal tissue or cells.

In the present invention, the "specimen" refers to tissue or cells of a lesion collected from a human or a tissue section or cells collected from a transplant site in a laboratory animal transplanted with tissue or cells derived from a lesion of a human. The "specimen" is usually in the form of a sample slide prepared in accordance with a predetermined procedure, such as one conventionally used to evaluate the expression of a target protein by immunostaining.

(Laboratory Animal)

In the present invention, a preferred specific example of a laboratory animal is one transplanted with the tissue of lesion of a human or cells derived therefrom. For example, when the lesion of a human (patient) is tumor, the laboratory animal may be one transplanted with tumor tissue or cancer cells collected from a tumor site or one transplanted with cultured cells obtained by cloning collected tumor tissue or cancer cells. In other words, in such a case, the "laboratory animal" is a tumor-bearing animal. Further, in addition to that, various laboratory animals such as lesion model animals, for example, Alzheimer's disease model animals, diabetes model animals, genetic disease model animals, and infectious disease model animals can be used depending on the purpose. Examples of animal species include those that are genetically controlled to some extent and have homogeneous genetic traits, such as mice, rats, rabbits, guinea pigs, gerbils, hamsters, ferrets, dogs, miniature pigs, monkeys, cows, horses, and sheep. From the viewpoint of ease in breeding and performing experiments, mice are particularly widely used.

When a tumor-bearing animal is used as a laboratory animal, a technique for retaining a tumor site in the laboratory animal is not particularly limited, and a known technique may be used. For example, various techniques have been tried, such as one in which the body of a mouse is incised and a tumor block of a patient is transplanted into the mouse and one in which tumor tissue collected from a patient or cultured cells derived therefrom is or are inserted by injection.

(Tumor-Bearing Mouse)

When a tumor-bearing animal is used as a laboratory animal in the present invention, a tumor-bearing model mouse is preferably used, and a PDX model mouse that will be described later is more preferably used. The tumor-bearing model mouse can broadly be classified into three types: a naturally induced tumor-bearing mouse; a cultured cancer cell-transplanted mouse; and a patient-derived tumor tissue-transplanted mouse (see Table 1; Kohrt et al., Defining the optimal murine models to investigate immune checkpoint blockers and their combination with other immunotherapies. Annals of Oncology 00: 1-9, 2016).

A cultured cancer cell-transplanted mouse is produced by transplanting cultured cells cloned by culturing tumor cells collected from a human (patient) in a test tube into a mouse with acquired immune deficiency. An example of the cultured cancer cell-transplanted mouse is a CDX [Cell-line derived xenograft] model mouse. Examples of a mouse transplanted within tumor tissue collected from a human (patient) include a PDX [Patient derived xenograft] model mouse, an Immuno-avatar model mouse, a hemato-lymphoid humanized model mouse, and an Immune-PDX model mouse.

with patient-derived tumor tissue (0th generation); a first generation mouse in which a tumor site of the 0th generation mouse has been transplanted (passaged); and an n+1th generation mouse after the first generation mouse, in which a tumor site of the nth generation (n≥1) mouse has been transplanted (passaged).

Therefore, when a tumor-bearing mouse is used as a laboratory animal in the present invention, the "specimen" may be prepared from a site, in which tumor cells or tumor tissue have or has been transplanted to produce the tumor-bearing mouse, after a certain period of time from transplantation.

(Specific Biomarker)

In the present invention, the "specific biomarker" refers to a biological substance (e.g., protein, nucleic acid) present in the lesion of a human, and preferably refers to a biological substance expressed by cells contained in the lesion of a human, and typically refers to a biological substance that is specifically expressed in cells contained in diseased tissue.

The specific biomarker can be identified on the basis of genetic mutation information obtained by performing gene analysis of a specimen prepared from a lesion (diseased tissue) collected from a patient by a genetic test and analyzing genetic mutation information of the specimen. For example, when a protein coded by a mutated gene is identified as a specific biomarker, the efficacy of a molecularly targeted drug that targets the specific biomarker can be estimated by acquiring and analyzing information about the specific biomarker.

More specifically, tumor tissue or the like collected from a patient is used to analyze the genetic mutation information thereof, and a protein coded by a mutated gene is identified as a specific biomarker. Further, part of the tumor tissue or the like is transplanted into a laboratory animal, and after a

TABLE 1

| | Cancer cells | Immune cells | Model |
| --- | --- | --- | --- |
| Naturally induced tumor-bearing mice | Murine | Murine | Classis model produce by transplanting a carcinogen compound<br>*Genetic-engineered mouse model<br>*Human KI mice |
| Cultured cancer cell-transplanted mice | Murine | Murine | (3) Syngeneic murine model |
| | Human | Murine | (4) Cell-line derived xenograft (CDX) |
| Patient-derived tumor tissue-transplanted mice | Human | Murine | (5) Patient derived xenograft (PDX)<br>(6) Immuno-avatar mice<br>(7) Hemato-lymphoid humanized mice<br>(8) Immune-PDX |

*gene knock-in mouse

A PDX mouse is produced by transplanting tumor tissue derived from a patient in a mouse with acquired immune deficiency. An Immuno-avatar model mouse, a Hemato-lymphoid humanized model mouse, or an Immune-PDX model mouse is produced by transplanting tumor tissue derived from a patient into a mouse with acquired immune deficiency transplanted with human peripheral-blood mononuclear cells, CD34+ human hematopoietic stem cells and progenitor cells thereof (HSPC), or tumor-infiltrating lymphocytes, respectively.

The term "patient-derived tumor tissue-transplanted mouse" includes all of the following mice: a mouse that has been grown for a certain period of time after transplanted lapse of an appropriate time, information about the specific biomarker in the transplant site is analyzed, a molecularly targeted drug that targets the specific biomarker is administered to the laboratory animal, and acquired information about the expression status of the biomarker and acquired medical information about the effect of the drug are linked together. In this way, the effect of the drug at the time when the drug is actually administered to the patient can be estimated.

In the present invention, the specific biomarker is not particularly limited as long as it is present in the specimen, and one specific type of biological substance present in the specimen may be selected as a specific biomarker, or two or more types of biological substances may be selected as specific biomarkers.

When the specific biomarker is nucleic acid, the nucleic acid is preferably RNA derived from the genome of cells contained in the tissue of a lesion (diseased tissue), such as mRNA, tRNA, miRNA, siRNA, or non-cording-RNA, particularly preferably miRNA such as miR21, miR34a, miR197, miR200, miR513, miR-133a, miR-143, exosomal micro-RNA (miR-181c, miR-27b), let-7a, miR-122, or iR4717.

When the specific biomarker is a protein, the protein is preferably one that is to be phosphorylated in cells contained in the tissue of a lesion (diseased tissue). Examples of such a protein to be phosphorylated include HER2, HER3, EGFR, and VEGFR. When the protein to be phosphorylated is used as a specific biomarker, information about the specific biomarker may include information about the total expression level of the protein, the ratio of the phosphorylated type of protein to the total expression level of the protein, and the amount of only the phosphorylated type of protein.

When the specimen is derived from tumor tissue or a tumor site, cells contained therein include not only tumor cells but also cells other than the tumor cells, such as immune cells that interact with the tumor cells. Therefore, the specific biomarker in this description is preferably a cancer-associated protein expressed in tumor cells and/or a protein expressed in immune cells.

(Cancer-Associated Protein)

Typical examples of the "cancer-associated protein" include "immune-related proteins expressed in cancer cells", "pathway-related proteins expressed in cancer cells", and metastasis-related proteins expressed in cancer cells". Various cancer-associated proteins are known, each of which is classified into any one of the above types. The cancer-associated protein is not particularly limited, and an appropriate cancer-associated protein can be selected depending on the purpose of diagnosis or treatment or the action mechanism of a drug to be used. It is to be noted that proteins coded by genes of an immune-related (Immune) gene panel, a pathway-related (Pathway) gene panel, and a metastasis-related (Progression) gene panel (each of which covers 770 genes) included in cancer-associated gene expression panels provided by nCounter correspond to the immune-related proteins expressed in cancer cells, the pathway-related proteins expressed in cancer cells, and the metastasis-related proteins expressed in cancer cells, respectively. Further, mutant proteins corresponding to the mutant genes of these genes may also be included in the immune-related proteins, the pathway-related proteins, and the metastasis-related proteins.

Examples of the "immune-related proteins expressed in cancer cells" include immune checkpoint proteins such as CD40, TL1A, GITR-L, 4-188-L, CX4D-L, CD70, HHLA2, ICOS-L, CD85, CD86, CD80, MHC-II, PDL1, PDL2, VISTA, BTNL2, B7-H3, B7-H4, CD48, HVEM, CD40L, TNFRSF25, GITR, 4-188, OX40, CD27, TMIGD2, ICOS, CD28, TCR, LAG3, CTLA4, PD1, CD244, TIM3, BTLA, CD160, and LIGHT.

Examples of the "pathway-related proteins expressed in cancer cells" include: cancer cell growth factors or cancer cell growth factor receptors such as EGFR(HER1), HER2, HER3, HER4, IGFR, and HGFR; cell surface antigens, vascular growth factors, or vascular growth factor receptors such as VEGF-A, VEGF-B, VEGF-C, VEGF-D, VEGF-E, PIGF-1, and PIGF-2; cytokines or cytokine receptors such as interferons, interleukins, G-CSF, M-CSF, EPO, SCF, EGF, FGF, IGF, NGF, PDGF, and TGF.

Examples of the "metastasis-related proteins expressed in cancer cells" include cancer metastasis markers such as ACTG2, ALDOA, APC, BRMS1, CADM1, CAMK2A, CAMK2B, CAMK2D, CCL5, CD82, CDKN1A, CDKN2A, CHD4, CNN1, CST7, CTSL, CXCR2, YBB, DCC, DENR, DLC1, EGLN2, EGLN3, EIF4E2, EIF4EBP1, ENO1, ENO2, ENO3, ETV4, FGFR4, GSN, HK2, HK3, HKDC1, HLA-DPB1, HUNKIL11, KDM1A, KISS1, LDHA, LIFR, MED23, MET, MGAT5, MAP2K4, MT3, MTA1, MTBP, MTOR, MYCL, MYH11, NDRG1, NF2, NFKB1, NME1, NME4, NOS2, NR4A3, PDK1, PEBP4, PFKFB1, PFKFB4, PGK1, PLAUR, PTTG1, RB1, RORB, SET, SLC2A1, SNRPF, SSTR2, TCEB1, TCEB2, TCF20, TF, TLR4, TNFSF10, TP53, TSHR, MMP, MMP2, MMP10, and HIF1.

(Proteins in Immune Cells)

Examples of the "protein expressed in immune cells" include PD-1, CTLA-4, TIM3, Foxp3, CD3, CD4, CD8, CD25, CD27, CD28, CD70, CD40, CD40L, CD80, CD86, CD160, CD57, CD226, CD112, CD155, OX40(CD134), OX40L(CD252), ICOS(CD278), ICOSL(CD275), 4-1BB (CD137), 4-1BBL(CD137L), 2B4(CD244), GITR(CD357), B7-H3(CD276), LAG-3(CD223), BTLA(CD272), HVEM (CD270), GITRL, Galectin-9, B7-H4, B7-H5, PD-L2, KLRG-1, E-Cadherin, N-Cadherin, R-Cadherin, IDO, TDO, CSF-1R, HDAC, CXCR4, FLT-3, and TIGIT.

(Proteins Contained in Stroma)

The specific biomarker in this description may be one expressed in cells other than tumor cells and immune cells. Specific examples of a biological substance expressed in cells other than tumor cells and immune cells include proteins contained in stroma.

The "stroma" is mainly composed of stromal cells such as fibroblasts, endothelial cells, and leucocytes (lymphocytes, monocytes, neutrophils, eosinophils, basophils) and an extracellular matrix composed of proteins such as collagen and proteoglycan. A biological substance present in either of stromal cells and an extracellular matrix may be used as a specific biomarker. However, a biological substance expressed by stromal cells is preferably selected as a specific biomarker because such a biological substance is considered to have a greater influence on the characters of a transplanted lesion (e.g., tumor cells) carried by a laboratory animal. More preferably, a biological substance expressed by fibroblasts as representative stromal cells is selected.

As the protein contained in stromal cells, for example, an appropriate one can be used which is selected from the following membrane proteins as stromal cell markers. Particularly, CD140a is preferred as a stromal cell marker in the present invention, which is a membrane protein expressed on the surface of cells such as fibroblasts, megakaryocytes, monocytes, erythrocytes, myeloid precursor cells, and endothelial cells.

Hereinbelow, specific examples of stroma cell markers and their respective main distributions will be described.

CD106 (VCAM-1, INCAM-110) . . . activated vascular endothelial cells, dendritic cells;

CD109 (Platelet activation factor, 8A3, E123) . . . activated T cells, platelets, vascular endothelium, megakaryocytes, CD34+ progenitor cell subsets;

CD140a (PDGF-R, PDGFR2) . . . fibroblasts, megakaryocytes, monocytes, erythrocytes, myeloid precursor cells, endothelial cells CD140b (PDGF-R, PDGFR1) . . . endothelial cells, stromal cells; CD141 (Thrombomodulin) . . . vascular endothelium, myeloid cells, platelets, smooth muscles CD142 (Tissue Factor (TF), Thromboplastin) . . . epithelial cells, activated monocytes, activated vascular endothelium;

CD143 (ACE: angiotensin-converting enzyme) . . . vascular endothelium, epithelial cells, activated macrophages;

CD144 (VE-Cadherin, Cadherin-5) . . . vascular endothelium;

CD145 (7E9, P7A5) . . . endothelial cells;

CD146 (MUC18, s-endo, Mel-CAM) . . . vascular endothelium, activated T cells, melanoma;

CD147 (Basigin, M6, EMMRRIN) . . . leucocytes, erythrocytes, vascular endothelium, platelets;

CD201 (EPCR: vascular endothelial cell protein C receptor) . . . vascular endothelium;

CD202 (TIE2, TEK) . . . vascular endothelium, hematopoietic stem cell subsets;

CD280 (Endo180, TEM22, uPARAP (uPAR-associated protein)) . . . myeloid precursor cells, fibroblasts, endothelial cell subsets, macrophage subsets;

CD299 (DC-SIGN-related, L-SIGN(Liver/Lympho node specific ICAM3-grabbing nonintegrin)) . . . endothelial cells;

CD309 (VEGFR2 (Vascular endothelial growth factor receptor 2), KDR) . . . endothelial cells, megakaryocytes, platelets, stem cell subsets;

CD322 (JAM2(Junctional adhesion molecule 2)) . . . endothelial cells, monocytes, B cells, T cell subsets;

CD331 (FGFR1 (Fibroblast growth factor receptor 1)) . . . fibroblasts, epithelial cells;

CD332 (FGFR2, Keratinocyte growth factor receptor) . . . epithelial cells;

CD333 (FGFR3, JTK4) . . . fibroblasts, epithelial cells;

CD334 (FGFR4, JTK2, TKF) . . . fibroblasts, epithelial cells;

CD339 (Jagged-1, JAG1) . . . stromal cells, epithelial cells (Expression Status of Specific Biomarker)

In the present invention, the expression status of the specific biomarker refers to characteristics provided by information such as the expression level of the specific biomarker, the type, number, and/or morphology of cells expressing the specific biomarker, and the expression site of the specific biomarker (when a tumor-bearing animal model is used as a laboratory animal, distribution in tumor tissue or a tumor site, occupied area).

(Information about Expression Status of Specific Biomarker)

In the method according to the present invention, examples of the information about the expression status of the specific biomarker include: (1) the expression level of the specific biomarker per cell or per unit area of tissue; (2) a histogram showing the expression level of the specific biomarker per cell and the number of cells corresponding thereto; (3) a curve showing the expression level of the specific biomarker per cell and the number of cells corresponding thereto; (4) information about the mutual positional information (distance) of the specific biomarkers; and (5) information about patterns such as the localization pattern of the specific biomarker in cells and the localization pattern of a specific cell group (e.g., a cancer cell group) in a region of interest(ROI), in a specimen (sample slide). Such information is preferably one acquired as image information (including one converted as a digital image), more preferably one that can be converted as quantitative information. The information about expression status may be any one of the above-described pieces of information or a combination of two or more of the above-described pieces of information. Further, two or more specific biomarkers may be selected, in which case the information about expression status may be a combination of their respective pieces of information about expression status.

A method for acquiring information about the expression status of the specific biomarker as image information is not particularly limited. For example, image information converted as a digital image can be acquired by capturing an image of a specimen (sample slide) using a high-resolution whole slide scanner, and information about the expression status of the specific biomarker can be quantitatively analyzed by image analysis of the image information. This analysis may be performed using any algorithm generally used for processing or analysis of digital images or may be performed using an algorithm optimized depending on the specific biomarker or an object to be detected.

In order to quantitatively acquire information about expression status from image information, a technique is used in which the specific biomarker is labeled by staining a specimen (sample slide) typically using particles having a nano-sized diameter such as an organic fluorochrome, quantum dots, or phosphor integrated dots (PIDs) that are particles obtained by integrating a phosphor such as an organic fluorochrome or quantum dots in a matrix such as a resin. Particularly, a staining method (PID method) performed using phosphor integrated dots is preferably used in the present invention. However, the technique used in the present invention is not particularly limited thereto, and another technique comparable in accuracy to the PID method may be used. As described above, basic embodiments of the PID method are known from a plurality of Patent Literatures and Non-Patent Literatures. Also in Examples in this description, information about expression status was acquired by the PID method performed according to an embodiment in which pathological diagnosis is performed using a sample slide. Hereinbelow, a method for acquiring information about the expression status of the specific biomarker by the PID method will be described in detail as an embodiment of the present invention.

(1) When the specific biomarker is, for example, a protein and the average expression level of the protein per cell is quantified, for example, a specimen (sample slide) is subjected to fluorescent immunostaining using a phosphor integrated dot-bound anti-specific biomarker antibody, and the stained sample slide is observed and imaged by irradiation with excitation light having a wavelength corresponding to the phosphor integrated dots used so that an image can be obtained in which the phosphor integrated dots labeling the specific biomarker are shown as bright spots. The number of the bright spots in the obtained fluorescently-stained image may be used as an index value of the expression level of the specific biomarker. There is a case where two or more phosphor integrated dots constitute one bright spot, in which case the number of phosphor integrated dots contained in a certain bright spot can be calculated by dividing the brightness (luminance, fluorescence intensity) of the bright spot by brightness per phosphor integrated dot separately measured in advance. The thus calculated number of particles may be used as an index value of the expression level of the specific biomarker.

Similarly, when the expression level of the specific biomarker per unit area of tissue is determined, the number of bright spots or the number of particles in cells contained in tissue present in a specific region in the image is counted and then divided by the area of the tissue.

The number of cells contained in the entire image or a specific region (e.g., only tumor tissue) in the image can be counted by performing, in addition to the above-described fluorescent immunostaining, staining using a staining agent for morphological observation (e.g., eosin) so that the shape of cells can be identified and then by performing observation and imaging in a bright field. By overlaying the two images, that is, the fluorescently-stained image and the stained image for morphological observation by image processing, the number of bright spots or particles indicating the specific biomarker expressed in each of the cells can be counted. As an index of the expression level of the specific biomarker, an average expression level per cell may be used which is calculated by dividing the number of bright spots or particles contained in the entire image by the number of cells, or an average value may be used which is calculated by counting the number of bright spots or particles contained in each of the cells.

When the specific biomarker is nucleic acid, the expression level per cell or unit area can be determined in the same manner except that, instead of the immunostaining, a method is used in which a gene is specifically stained using a phosphor integrated dot-labeled probe (e.g., FISH method).

(2) When a histogram showing the expression level of the specific biomarker per cell and the number of cells corresponding thereto is produced, first, in the same manner as in (1), the number of bright spots or particles indicating the expressed specific biomarker is determined per cell contained in the entire image or a specific region (e.g., only tumor tissue). Then, the expression level of the specific biomarker per cell is divided into sections every predetermined number of bright spots or particles (e.g., as performed in Examples described in this description, the number of particles per cell from 1 to 300 is divided every 20 particles into 16 sections including the section of 0 particles) and plotted on the horizontal axis and the number of cells (frequency) corresponding to each of the sections is counted and plotted on the vertical axis. In this way, the histogram can be produced.

(3) When a curve showing the expression level of the specific biomarker per cell and the number of cells corresponding thereto is produced, first, in the same manner as in (2), the number of bright spots or particles indicating the expressed specific biomarker is determined per cell contained in the entire image or a specific region (e.g., only tumor tissue) in the image. Then, the expression level of the specific biomarker per cell is continuously plotted on the horizontal axis (without dividing into sections unlike the case of the histogram), and the number of cells (frequency) corresponding to each expression level is counted and plotted on the vertical axis. In this way, the curve can be produced.

From the histogram produced in (2) and the curve produced in (3), it is possible to acquire information such as the state of distribution (the shape of the histogram or curve, the number of peaks), the levels of an average value or a median value and a variance (CV), and particularly in the case of the histogram, the level of the number of cells (frequency) corresponding to the section of the largest number of bright spots or particles per cell. It is to be noted that the histogram and the curve are originally graphs obtained by measuring the expression level of the specific biomarker (the number of bright spots or the number of particles) and the number of cells expressing the specific biomarker and directly using these values, and are therefore categorized as information obtained not by a "qualitative" technique but by a "quantitative" technique.

(4) When mutual positional information (distance) of the two or more specific biomarkers is quantified, the distance between the phosphor integrated dots (bright spots) labeling the different specific biomarkers can be regarded as the distance between the different specific biomarkers. When this process is performed, fluorescent staining for one specific biomarker and fluorescent staining for another specific biomarker are performed on the same specimen (e.g., tissue slice) (multiple immunostaining). At this time, fluorescent labels that emit fluorescence of different wavelengths are appropriately used to distinguish the different specific biomarkers.

(5) When the localization pattern of the specific biomarker in cells is obtained, an image in which phosphor integrated dots labeling the specific biomarker are shown as bright spots (dark field image) and an image in which cells are stained to identify the shape of the cells (bright field image) are overlaid by image processing to obtain an image showing the distribution of the biomarker in each of the cells, and the distribution state of the specific biomarker is classified into any several patterns(e.g., accumulation in the center of the cell, accumulation in the periphery of the cell (in the vicinity of the cell membrane, diffusion throughout the cell). The most major localization pattern among all the localization patterns of cells contained in the image may be determined and regarded as the localization pattern of the specific biomarker in the specimen (tissue). In order to obtain a localization pattern in a region of interest (ROI), a region as a region of interestis set in the image obtained by overlaying the bright field image and the dark field image, and a localization pattern of a specific cell group (e.g., a cancer cell group) contained in the region of interest is classified.

(Determination of Efficacy of Therapeutic Method and Selection of Therapeutic Method)

According to one aspect of the present invention, it is possible to estimate therapeutic efficacy in a patient with a high degree of accuracy by identifying a specific biomarker on the basis of mutation information acquired by gene analysis of a lesion (diseased tissue) collected from the patient as a specimen, further by associating information (including image information) about the expression status of the specific biomarker in the diseased tissue of a laboratory animal transplanted with the lesion and an analysis result thereof with medicinal information such as the effect or side effect of a therapy (drug) in the laboratory animal and prognosis for the laboratory animal to acquire a set of information, and by analyzing it from many directions.

A disease to be treated is not particularly limited, examples thereof include a neurological disease, an infectious disease, a genetic disease, and a tumor (cancer), and a typical example thereof is a tumor (cancer). The tumor is not particularly limited, and examples thereof include solid cancers such as cytoma, melanoma, sarcoma, brain tumor, head and neck cancer, stomach cancer, lung cancer, breast cancer, liver cancer, colorectal cancer, cervical cancer, prostate cancer, and bladder cancer, leukemia, lymphoma, and multiple myeloma.

A therapeutic method is not particularly limited as long as it is used for a disease to be treated. For example, when the disease is a tumor, examples of a therapeutic method therefor include surgery, radiation therapy (heavy particle radiation therapy, proton radiation therapy), and medication therapy. Typically, medical therapy is used such as administration of an anticancer drug, a hormonal agent, or an immunostimulant. Particularly, a molecularly targeted drug whose target molecule is a specific biomarker (for example, an antibody drug that recognizes the biomarker or an ADC (antibody-drug conjugate) drug) is preferably used.

Hereinbelow, a method for estimating the efficacy of a tumor therapy using a drug will be described, but the present invention is not particularly limited to this embodiment.

A specific biomarker is identified by gene analysis of a lesion (tumor tissue) collected from a patient as a specimen. Further, the lesion is transplanted into a laboratory animal, and the transplanted lesion is collected as a specimen after a lapse of an appropriate time to acquire information about the expression status of the specific biomarker. The efficacy of a drug that targets the specific biomarker is evaluated on the basis of the information about expression status and an analysis result thereof. For example, when the specific biomarker as a target for the drug is not expressed in the diseased tissue or the specific biomarker is expressed in the diseased tissue but the ratio of cells expressing the specific biomarker is small, it is possible to estimate that even when the therapy is actually performed (even when the drug is actually administered), its effect cannot be expected.

Further, a higher-accuracy estimated result can be obtained by performing, before administration of the drug to the patient, a surrogate test in which the drug is administered to the above-described laboratory animal (e.g., a PDX mouse) transplanted with a lesion collected from the patient to evaluate the effect or side effect or the like of the drug.

A method for evaluating the effect of the drug is not particularly limited. For example, a change in the size of a transplanted lesion (tumor) before and after the administration of the drug may be used as an index, or the value of a known tumor marker, an infectious disease marker, or the like in the blood or the result (change) of another pathological test may be used as an index. A method for evaluating the side effect or the like is not particularly limited, but the value of blood cells or the result of pathological tissue examination of a digestive canal or the like can be used as an index.

(Provision of Information as Database)

According to another aspect of the present invention, it is possible to provide one or more pieces of information including information about the expression status of a specific biomarker to estimate or evaluate therapeutic efficacy. More specifically, when an information group including information about the expression status of a specific biomarker, an analysis result thereof, medicinal information, and other information is provided as an integrated database to, for example, medical institutions and companies, the database can be effectively used in various situations such as estimation of the effect of a disease therapeutic method or a drug, a drug trial, a clinical trial, and development of a therapy plan. Such information may include disclosed known information, and may include information acquired by performing fluorescent immunostaining using fluorescent nanoparticles on various specimens. Hereinbelow, construction and utilization form of a database using PDX mice will be described, but are not particularly limited.

Under a certain protocol, tumor tissues are collected from PDX mice to prepare specimens (sample slides). The tumor tissues are genetically analyzed. On the basis of information about a genetic mutation occurring in the tumor tissues, a protein associated with the mutation information, for example, a protein coded by a mutated gene is identified as a specific biomarker. Further, fluorescent immunostaining is performed to label the specific biomarker with PIDs to image the expression status of the specific biomarker in the specimens, and image information is analyzed to acquire information about expression status.

Examples of medicinal information include information acquired by evaluating the effect of a drug by a means such as measurement of tumor volumes before and after administration of the drug to the PDX mice, and information acquired by determining the presence or absence of a side effect by sampling the digestive canal, blood, and behavior of the PDX mice. The drug to be administered may be a single drug or a combination of two or more drugs. Further, more detail information can be acquired by changing dosage form, route of administration, duration of administration, and frequency of administration.

The genetic (mutation) information, information about the expression status of a biomarker, and the medicinal information acquired from the PDX mice bearing tumor tissues derived from various patients are integrated by the above described procedure to construct a database.

Such a database can be provided so that users can use it through a network, or can be provided to users by storing it in computer-readable recording media such as optical memory discs (e.g., compact discs (CDs), digital versatile discs (DVDs)) and flash memories (e.g., solid state drives (SSDs), memory cards).

(Utilization of Database-1)

For example, the expression status of a specific biomarker in a specimen collected from a patient or a specimen of a PDX mouse transplanted with tissue collected from a patient is checked against the above-described database, and one or more samples whose information about expression status is similar thereto are extracted from the database so that the effect or side effect a drug can be estimated before the drug is administered to the patient by reference to medicinal information included in the sample(s).

Further, the effect or the like of the drug can be estimated with a higher degree of accuracy by performing, before the drug is actually administered to the patient, a surrogate test in which the drug is administered to the PDX mouse. Further, the amount of information of the database can be increased by storing information by further adding information about the expression status of the specific biomarker and medicinal information acquired from the PDX mouse to the database, which makes it possible to increase the accuracy of information to be provided.

(Utilization of Database-2)

Further, PDX mice and a database thereof can be effectively used in a drug trial or a clinical trial. For example, in the case of a drug trial, there are three (1 to 3) stages called phases. In each of the stages, the safety or efficacy of a drug is confirmed. The degree of expectation of drug efficacy or a possible risk can be estimated by producing PDX mice and performing a test on the PDX mice before a drug candidate is actually administered to patients (humans). Hereinbelow, a specific example thereof will be described.

PDX mice are produced by transplanting mice with acquired immune deficiency with tumor tissues collected from cancer patients to be administered a candidate therapeutic drug who are participant candidates of a drug trial. Information about the expression status of a specific biomarker as a target molecule of the candidate therapeutic drug in each of the PDX mice is acquired, and medical information is acquired by administering the candidate therapeutic drug to each of the mice. From such information, it is possible to estimate the degree of drug efficacy expected by administration of the candidate therapeutic drug and a possible side effect or the like for each of the patients.

The expression status of a specific biomarker in a specimen collected from a patient as a subject of a drug trial or a specimen collected from a PDX mouse transplanted with tissue collected from the patient is checked against a database, and one or more samples whose information about expression status is similar thereto are extracted from the database, and the expected effect or risk of a drug is estimated on the basis of medicinal information included in the sample(s). This makes it possible to determine whether or not the patient is suitable as a subject and perform a drug trial more efficiently with less risk. The amount of information of the database can be increased by storing information by further adding, to the database, the information about the expression status of the specific biomarker and the medicinal information acquired from the PDX mouse in such a manner as described above, which makes it possible to increase the accuracy of information to be provided. The database can be used to estimate the effect of the drug or a possible side effect at the time when medication is actually performed as a therapeutic tool.

(Utilization of Evaluation Model-3)

Further, in the case of a field whose database has many samples, that is, a field where there are many target patients (e.g., breast cancer or lung cancer), the database can be used to determine the therapeutic strategy of a certain patient. For example, information about the expression status of various specific biomarkers (e.g., a plurality of cancer-associated proteins or nucleic acids) is acquired from a specimen collected from a certain cancer patient or a specimen collected from a PDX mouse transplanted with tissue collected from the patient and is checked against a database to extract a sample whose information about expression status is similar thereto, which makes it possible to estimate that which drug is effective for the tumor tissue and how the drug should be administered to obtain the effect of the drug.

Further, a plurality of PDX mice derived from the patient are produced, and candidate drugs are administered to the PDX mice by various methods to evaluate the effects or the like of the drugs, which makes it possible to more efficiently determine a drug to be actually administered and make a dosage schedule. Further, the amount of information of the field included in the database can further be increased by storing information by further adding, to the database, information about the expression status of the specific biomarkers and medicinal information acquired by the above method which makes it possible to make an estimate with a higher degree of accuracy.

EXAMPLES

[Production Example 1] Production of Biotin-Modified Anti-Rabbit IgG Antibody

In a 50 mM Tris solution, 50 μg of an anti-rabbit IgG antibody used as a secondary antibody was dissolved. A DTT (dithiothreitol) solution was added to and mixed with the resulting solution so that a final concentration was 3 mM, and the mixture was reacted at 37° C. for 30 minutes. Then, the reaction solution was passed through a desalting column "Zeba Desalt Spin Columns" (Cat. #89882 manufactured by Thermo Fisher Scientific Inc.) to purify the secondary antibody reduced with DTT. Then, 200 μL of the total amount of the purified antibody was dissolved in a 50 mM Tris solution to prepare an antibody solution. At the same time, a linker reagent "Maleimide-PEG2-Biotin" (product number: 21901, manufactured by Thermo Fisher Scientific Inc.) was adjusted to 0.4 mM with DMSO. Then, 8.5 μL of the linker reagent solution was added to and mixed with the antibody solution, and the mixture was reacted at 37° C. for 30 minutes to bind biotin to the anti-rabbit IgG antibody via a PEG chain. This reaction solution was purified by passing it through a desalting column. The absorbance of the desalted reaction solution at a wavelength of 300 nm was measured using a spectrophotometer ("F-7000" manufactured by Hitachi, Ltd.) to calculate the concentration of the protein (biotin-modified secondary antibody) in the reaction solution. A solution prepared by adjusting the concentration of the biotin-modified secondary antibody to 250 μg/mL using a 50 mM Tris solution was used as a solution of the biotin-modified secondary antibody.

[Production Example 2] Production of Texas Red Integrated Melamine Resin Particles In 22.5 mL of pure water, 2.5 mg of Texas Red dye molecules "Sulforhodamine 101" (manufactured by Sigma-Aldrich) was dissolved. Then, the resulting solution was stirred for 20 minutes by a hot stirrer while the temperature of the solution was maintained at 70° C. The solution after stirring was mixed with 1.5 g of a melamine resin "NIKA-LAC MX-035" (manufactured by NIPPON CARBIDE INDUSTRIES CO., INC.) and further heated and stirred for 5 minutes under the same conditions. The solution after stirring was mixed with 100 μL of formic acid and stirred for 20 minutes while the temperature of the solution was maintained at 60° C., and was then allowed to stand to be cooled to room temperature. The solution after cooling was dispensed into tubes for centrifugation and centrifuged at 12,000 rpm for 20 minutes to precipitate Texas Red integrated melamine resin particles contained in the solution as a mixture. Supernatant was removed, and the precipitated particles were washed with ethanol and water. Then, 1000 of the obtained particles were observed with a SEM, and the average particle diameter thereof was measured and found to be 152 nm. The thus produced Texas Red integrated melamine resin particles were surface modified with streptavidin according to the following procedure, and the thus obtained streptavidin-modified Texas Red integrated melamine resin particles were used as phosphor integrated dots (PIDs) in Examples 1 and 3.

[Production Example 3] Production of Streptavidin-Modified Texas Red Integrated Melamine Resin Particles First, 0.1 mg of the particles obtained in Production Example 2 was dispersed in 1.5 mL of EtOH, 2 μL of aminopropyltrimethoxysilane "LS-3150" (manufactured by Shin-Etsu Chemical Co., Ltd.) was added thereto, and the mixture was reacted for 8 hours to perform surface amination treatment.

Then, PBS (phosphate buffered saline) containing 2 mM EDTA (ethylenediaminetetraacetic acid) was used to prepare a solution containing the particles subjected to surface amination treatment at a concentration of 3 nM, the solution was mixed with SM(PEG)12 (succinimidyl-[(N-maleimido-propionamido)-dodecaethyleneglycol]ester, manufactured by Thermo Fisher Scientific) so that the final concentration of SM(PEG)12 was 10 mM, and the mixture was reacted for 1 hour. The mixture was centrifuged at 10,000 G for 20 minutes, a supernatant was removed, PBS containing 2 mM EDTA was then added thereto to disperse a precipitate, and centrifugation was again performed. Washing by the same procedure was performed three times to obtain Texas Red integrated melamine resin particles having terminal maleimide groups.

At the same time, streptavidin (manufactured by Wako Pure Chemical Industries, Ltd.) was subjected to thiol group addition treatment by performing reaction with N-succinimidyl S-acetylthioacetate (SATA) and then deprotection. The resulting reaction liquid was filtered through a gel filtration column to obtain a solution of streptavidin capable of binding to Texas Red integrated melamine resin particles.

The above-described Texas Red integrated melamine resin particles and streptavidin were mixed in PBS containing 2 mM EDTA and reacted at room temperature for 1 hour. Then, 10 mM mercaptoethanol was added to terminate the reaction. The obtained solution was concentrated with a centrifugal filter, and then unreacted streptavidin etc. were removed using a gel filtration column for purification to prepare streptavidin-modified Texas Red integrated melamine resin particles.

Preparation for Evaluation-1

Each of breast cancer tissues of five breast cancer patients (A to E) was subjected to exhaustive gene analysis, and biomarkers were identified on the basis of obtained genetic mutation information. The identified biomarkers (specific biomarkers) were HER2 and ER. Further, cancer cells isolated from breast cancer tissue of each of the five patients were transplanted under the skin of SCID (Severe Combined ImmunoDeficiency) mice (five mice transplanted with tumor tissue derived from each patient were produced, and a total of 25 mice were produced). After the volume of tumor reached 100 mm$^3$ (about 3 months after transplantation), tail intravenous administration of trastuzumab (trade name: Herceptin) to these mice was started (15 mg/kg: once every 4 days: 4 times in total). The volume of tumor was measured before and after administration, and a tissue section (tumor tissue) was collected from each of the killed mice at each time point before initial administration and after 1 week, 2 weeks, 3 weeks, and 4 weeks from initial administration. Each of the collected tissue sections was subjected to formalin fixation and paraffin embedding according to conventional methods, and was further sliced to prepare two sample slides per mouse killed at each time point.

Example 1

(1) Immunostaining of HER2 Protein (1-1) Sample Slice Pretreatment

The sample slides prepared in Preparation for evaluation-1 were subjected to deparaffinization treatment and then washed with water. The washed sample slides were autoclaved in a 10 mM citrate buffer solution (pH6.0) at 121° C. for 15 minutes to perform antigen activation treatment. The tissue slides after activation treatment were washed with PBS, and the washed sample slides were subjected to blocking treatment for 1 hour using PBS containing 1% BSA.

(1-2) Fluorescent Immunostaining Step

The thus treated sample slides of each of the mice killed at each time point were subjected to immunostaining of the target protein HER2.

An anti-HER2 rabbit monoclonal antibody "4B5" (manufactured by Ventana) was diluted with PBS containing 1 W/W % BSA to a concentration of 0.05 nM, and the resulting solution was dropped onto each of the two sample slides prepared in the step (1) and corresponding to each of the patients (A to E) to perform reaction at 4° C. overnight. The solution of biotin-modified anti-rabbit IgG antibody prepared in Production Example 1 was further diluted with PBS containing 1 W/W % BSA to 6 µg/mL, and the resulting diluted solution was dropped onto the sample slides, washed with PBS after reaction, to perform reaction at room temperature for 30 minutes.

The streptavidin-modified Texas Red integrated melamine resin particles produced in Production Example 3 were diluted to 0.02 nM with a diluent for phosphor integrated dots (casein:BSA=5%), and the resultant was dropped onto the sample slides, washed with PBS after reaction, to perform reaction at room temperature for 3 hours in a neutral pH environment (pH 6.9 to 7.4).

(1-3) Staining Step for Morphological Observation

The sample slides subjected to fluorescent labeling treatment were subjected to hematoxylin staining using a Mayer's hematoxylin solution for 5 minutes and then washed with running water at 45° C. for 3 minutes.

(1-4) Sample Post-Treatment Step

The sample slides subjected to the above staining steps were subjected to fixation and dehydration treatment by repeating 4 times immersion in pure ethanol for 5 minutes. Then, clearing treatment was performed by repeating 4 times immersion in xylene for 5 minutes. Finally, sealing treatment was performed by applying a sealing agent "Entellan new" (manufactured by Merk) onto the samples and placing cover glasses thereon to prepare samples for use in observation.

(2) Evaluation of Expression Status of HER2 Protein (2-1) Observation and Imaging Step Irradiation with excitation light and observation of fluorescent emission in this step were performed using a fluorescence microscope "BX-53" (manufactured by Olympus Corporation), and capturing of fluorescently-immunostained images (400-fold) and stained images for morphological observation (400-fold) was performed using a digital camera for microscope "DP73" (manufactured by Olympus Corporation) attached to the fluorescence microscope.

First, each of the samples was irradiated with excitation light corresponding to Texas Red contained in the phosphor integrated dots used for staining of HER2 to emit fluorescence, and in this state, an immunostained image was captured. At this time, the wavelength of the excitation light was set to 575 to 600 nm using an optical filter for excitation light of the fluorescence microscope, and the wavelength of fluorescence to be observed was set to 612 to 692 nm using an optical filter for fluorescence. The intensity of the excitation light during observation and imaging with the fluorescence microscope was set so that irradiation energy near the center of the visual field was 900 W/cm$^2$. The exposure time during imaging was adjusted to fall within a range such that the brightness of an image to be captured was not saturated, and was set to, for example, 4000µ seconds.

Then, observation and imaging were performed in the bright field to capture hematoxylin-stained images for morphological observation.

Such capturing of fluorescently-immunostained images and stained images for morphological observation was performed in the same visual field, and then the same operation was repeated in different visual fields so that images were captured in five different visual fields per sample slide.

(2-2) Image Processing and Measurement Step

Image processing in this step was performed using image processing software "Image" (open source).

The stained image for morphological observation and the fluorescently-immunostained image were overlaid by image processing to extract bright spots indicating the Texas Red integrated melamine resin particles labeling HER2 expressed on the cell membrane. It is to be noted that HER2 is not expressed in the stromal cell region, and therefore bright spots located in stromal cells were processed as non-specific signals, that is, noise. The number of bright spots on the cell membrane having a brightness equal to or higher than a predetermined value was counted, and the brightness of the bright spots was divided by the brightness per particle of the above-described phosphor integrated dots (PIDs) to convert the brightness into the number of particles. The number of particles was taken as the expression level of HER2 in the cell. Then, the expression level of HER2 (number of particles) was measured for 1000 cells per sample slide (five visual fields), and the average thereof was calculated and taken as the "PID score" of the sample slide. Further, the average of PID scores of the two sample slides corresponding to each of the patients (A to E) was calculated.

Example 2

Immunostaining of ER and evaluation of expression status of ER were performed in the same manner as in the case of HER2 except that the anti-HER2 rabbit monoclonal antibody "4B5" used in (1-2) was changed to an anti-ER rabbit polyclonal antibody "ab180900 manufactured by Abcam".

(Results and Discussion)

The results of Examples 1 and 2 are shown in Table 2-1 and Table 2-2. It was confirmed that in the case of the PDX mice derived from the patients having a larger genetic mutation, the rate of HER2 protein reduction caused by drug administration was higher. Further, a change in the expression level of HER2 (PID score) was slightly different even between the patients A and B judged to be highly related to gene information and even between the patients C and D judged to be moderately related to gene information.

From the results, it is considered that drug efficacy in each patient can be estimated by performing a surrogate test using laboratory animals. For example, the size of tumor in the PDX mice corresponding to the patient A was reduced, and therefore there is a possibility that it can be estimated that therapeutic efficacy can be obtained by administering trastuzumab to the patient A. Similarly, it can be considered that in the case of the patient E, the effect of administration of trastuzumab cannot be expected. It can be considered that by estimating drug efficacy using PDX mice in such a manner as described above, it is possible to select or determine a therapeutic (medication) method suitable for each patient, such as a case where trastuzumab is selected as a therapeutic drug for the patient A, but another therapeutic drug is selected for and administered to the patient E, which makes it possible to make an efficient medication or therapy plan.

Further, by accumulating such gene information, medical information, information about expression status (PID score) and checking information of another patient against the accumulated information in the treatment of the patient, it is possible to suggest the possibility that the presence or absence of the efficacy of the drug in the patient can be determined.

TABLE 2-1

| | | | PID score (HER2) | | | |
|---|---|---|---|---|---|---|
| Patient | Number of copies of HER2 gene | Degree of genetic mutation | 1 week after administration | 2 weeks after administration | 3 weeks after administration | 4 weeks after administration |
| A | 23000 | high | 820 | 770 | 630 | 410 |
| B | 18000 | high | 530 | 400 | 350 | 350 |
| C | 11000 | middle | 1320 | 1210 | 1030 | 780 |
| D | 9800 | middle | 700 | 710 | 590 | 530 |
| E | 2800 | low | 590 | 610 | 580 | 550 |

TABLE 2-2

| | Degree of | PID score (ER) | | | |
|---|---|---|---|---|---|
| Patient | relation to gene information | 1 week after administration | 2 weeks after administration | 3 weeks after administration | 4 weeks after administration |
| A | high | 320 | 200 | 180 | 180 |
| B | high | 440 | 400 | 250 | 220 |
| C | middle | 320 | 210 | 130 | 150 |
| D | middle | 570 | 350 | 290 | 200 |
| E | low | 390 | 390 | 390 | 350 |

Preparation for Evaluation-2

Tumor tissues collected from four lung cancer patients (F, G, H, I) were subjected to gene analysis, and EGRF was identified as a specific biomarker. Further, tumor tissue was collected from each of the patients at the same time when drug administration was started, and a 2 mm-square piece of the tumor tissue was transplanted under the skin of SCID (Severe Combined ImminoDeficiency) mice (5 mice transplanted with tumor tissue derived from each patient were produced, and a total of 20 mice were produced). After the volume of tumor reached about 300 mm³ (about 1 month after transplantation), Gefitinib as an anti-human EGFR monoclonal antibody drug (trade name: Iressa) was tail-intravenously administered to each of the mice in an amount of 100 mg/kg twice a day 4 times in total. After 1 day and 100 days from the administration, tumor tissue was collected from the mice, and sample slides were prepared in the same manner as in Preparation for evaluation-1.

Example 3

Immunostaining of EGFR was performed, and observation, imaging, and image processing were further performed in the same manner as in the case of HER2 except that the anti-HER2 rabbit monoclonal antibody "4B5" (manufactured by Ventana) was changed to an anti-EGFR rabbit monoclonal antibody (clone "5B7" manufactured by Roche) to calculate the average PID score of each of the mice, and the localization status in cell was classified as any one of three localization patterns A to C.

The genetic mutation information and drug resistance to Gefitinib on day 100 after administration of each of the patients and the expression pattern of EGFR and the change in tumor volume of the corresponding mice at each time point are summarized in Table 3. In the case of the PDX mice transplanted with the tumor tissue of the patient F or H confirmed to have drug resistance on day 100 after drug administration, the volume of tumor was once reduced on day 100 after drug administration, but was increased thereafter. From this, it can be judged that resistance to Gefitinib was developed. Further, in the tumor tissues collected from these PDX mice, a change in the localizations status of EGFR was observed between day 1 and day 100 after administration of Gefitinib.

On the other hand, in the case of the PDX mice transplanted with the tumor tissue of the patient B or D confirmed to have no drug resistance on day 100 after drug administration, the volume of tumor was gradually reduced. From this, it can be judged that resistance was not developed, that is, drug efficacy was maintained. Further, in the sample slides prepared using the tumor tissues collected from these PDX mice, no change was observed in the localization status of EGFR.

Further, fluorescent immunostaining was performed in the same manner except that the anti-EGFR antibody was changed to an anti-mutated EGFR antibody. Also in this case, the same results were obtained, that is, a change in localization status was observed in the sample slides of mice derived from the patients F and H, but on the other hand, a change in localization status was not observed in the tissue slides of mice derived from the patients B and D. It is to be noted that when DAB staining was performed using an anti-mutated EGFR antibody, the localization status could not be observed due to low sensitivity.

(Discussion)

The above results reveal that the PDX mice produced using tumor tissues derived from the patients who have developed drug resistance develop drug resistance similarly to the patients. From this, it is considered that by administering a candidate therapeutic drug to a PDX mouse before it is actually administered to a patient, it may be possible to previously estimate whether the patient will develop drug resistance. Further, by accumulating information about the linkage between drug resistance (medical information) and expression of a specific biomarker, it is possible to estimate the possibility of development of drug resistance in a shorter period of time. For example, in the case of this Example, it can be expected that drug resistance will not be developed when a PDX mouse is confirmed to have no drug resistance and a change in the localization status of the specific biomarker (EGFR) is not observed on day 100 after drug administration. On the other hand, even when a PDX mouse is confirmed to have no drug resistance on day 100 after administration, it is estimated that there is a possibility that drug resistance is developed when a change in the localization status of the specific biomarker (EGFR) is observed. Therefore, it can be estimated that drug resistance will be developed also in a patient, and at this point of time, it may be possible to determine that another drug or therapeutic method is selected.

TABLE 3

| Patient information | | | | Murine information | | | |
| --- | --- | --- | --- | --- | --- | --- | --- |
| | Results of genetic test | | Drug resistance | PID staining of murine biopsy sample | | Change in tumor volume | |
| Patient | Exon 21 L858R mutation | T790M and C797S mutations | Day 100 after administration of Gefitinib | Day 1 after administration of Gefitinib | Day 100 after administration of Gefitinib | Day 100 after administration of Gefitinib | Day 200 after administration of Gefitinib |
| F | absent | present | developed | localization A | localization B | decreased | increased |
| G | absent | present | not developed | localization C | localization C | increased | decreased |
| H | absent | absent | developed | localization B | localization C | decreased | increased |
| I | absent | absent | not developed | localization B | localization B | decreased | decreased |

The invention claimed is:

1. A method comprising:

collecting a lesion from a human;

acquiring one or more first pieces of information including information about expression status of a specific biomarker by using, as a first specimen, the lesion collected from the human;

transplanting tissue of the lesion collected from the human or cells derived therefrom into a laboratory animal;

acquiring one or more second pieces of information including information about expression status of the specific biomarker by using, as a second specimen, a lesion collected from a transplant site in the laboratory animal transplanted with tissue of the lesion collected from the human or the cells derived therefrom; and using these first and second pieces of information thus acquired, in combination to estimate efficacy of a therapy, wherein the specific biomarker is a protein to be phosphorylated, a fluorescence image in which bright spots of phosphor integrated dots (PIDs) are shown is captured from the second specimen, the information about the expression status of the specific biomarker for the second specimen is acquired by analyzing image information from the fluorescence image, the information about the expression status of the specific biomarker for the second specimen is a PID score, and the information about expression status for the second specimen includes information about a vascular occupancy in the second specimen, wherein the specific biomarker is at least one selected from the group consisting of an immune checkpoint protein, a cancer cell growth factor, a cell surface antigen, a vascular growth factor, a vascular growth factor receptor, cytokine, and a cytokine receptor, and the information acquired in the laboratory animal is observation information of a localization status and drug resistance of the specific biomarker acquired by analyzing the image information of the fluorescence image in which bright spots of PIDs are represented, and predicting that there is a possibility that drug resistance will occur in the human when the observation information is observation information in which there is a change in the localization status and drug resistance has not been confirmed.

2. The method according to claim 1, further comprising identifying the specific biomarker via analysis of genetic mutation information of the first specimen.

3. The method according to claim 1, wherein the therapy is administration of a molecularly targeted drug that is a drug targeting the specific biomarker.

4. The method according to claim 3, wherein the molecularly targeted drug is an anticancer agent.

5. The method according to claim 1, wherein at least one of the lesion collected from the human and the lesion collected from the transplant site in the laboratory animal is a tumor.

6. A method comprising:

collecting a lesion from a human;

acquiring one or more first pieces of information including information about expression status of a specific biomarker by using, as a first specimen, the lesion collected from the human;

transplanting tissue of the lesion collected from the human or cells derived therefrom into a laboratory animal;

acquiring one or more second pieces of information including information about expression status of the specific biomarker by using, as a second specimen, a lesion collected from a transplant site in the laboratory animal transplanted with tissue of the lesion collected from the human or the cells derived therefrom; and using these first and second pieces of information thus acquired, in combination to estimate efficacy of a therapy, wherein the specific biomarker is a protein to be phosphorylated, a fluorescence image in which bright spots of phosphor integrated dots (PIDs) are shown is captured from the second specimen, the information about the expression status of the specific biomarker for the second specimen is acquired by analyzing image information from the fluorescence image, the information about the expression status of the specific biomarker for the second specimen is a PID score, and the information about expression status for the second specimen includes information about a vascular occupancy in the second specimen, wherein the specific biomarker is at least one selected from the group consisting of EGFR (HER1) and ER, and the information acquired in the laboratory animal is observation information of a localization status and drug resistance of the specific biomarker acquired by analyzing the image information of the fluorescence image in which bright spots of PIDs are represented, and predicting that there is a possibility that drug resistance will occur in the human when the observation information is observation information in which there is a change in the localization status and drug resistance has not been confirmed.

7. The method according to claim 1, wherein the information about expression status of the specific biomarker of at least one of the first specimen and the second specimen includes an expression level and an expression distribution of the specific biomarker.

8. The method according to claim 1, wherein an image information of at least one of the lesion collected from the human and the lesion collected from the transplant site in the laboratory animal is acquired by immunostaining using the PIDs.

* * * * *